(12) United States Patent
Ehrenfreund et al.

(10) Patent No.: US 7,582,589 B2
(45) Date of Patent: *Sep. 1, 2009

(54) 3-CARBONYLAMINOTHIOPHENES AND THEIR USE AS FUNGICIDES

(75) Inventors: Josef Ehrenfreund, Basel (CH); Harald Walter, Basel (CH); Hans Tobler, Basel (CH); Clemens Lamberth, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 216 days.

This patent is subject to a terminal disclaimer.

(21) Appl. No.: 10/554,336

(22) PCT Filed: Apr. 21, 2004

(86) PCT No.: PCT/EP2004/004194

§ 371 (c)(1),
(2), (4) Date: Aug. 14, 2006

(87) PCT Pub. No.: WO2004/099195

PCT Pub. Date: Nov. 18, 2004

(65) Prior Publication Data

US 2006/0276434 A1     Dec. 7, 2006

(30) Foreign Application Priority Data

May 7, 2003 (GB) .................................. 0310464.3
Aug. 12, 2003 (GB) .................................. 0318920.6
Mar. 3, 2004 (GB) .................................. 0404806.2

(51) Int. Cl.
*A01N 43/56* (2006.01)
*C07D 231/10* (2006.01)

(52) U.S. Cl. ............... 504/280; 548/356.1; 548/364.1; 548/365.7; 504/261

(58) Field of Classification Search ............... 548/356.1, 548/364.1, 365.7; 504/261, 280
See application file for complete search history.

(56) References Cited

FOREIGN PATENT DOCUMENTS

| | | | |
|---|---|---|---|
| WO | WO 96/18631 A | 6/1996 | |
| WO | WO 99/62915 A | 12/1999 | |
| WO | WO 2004/018438 A | 3/2004 | |

*Primary Examiner*—Golam M Shameem
(74) *Attorney, Agent, or Firm*—James Cueva

(57) ABSTRACT

The invention also relates to novel compounds of formula (1) where Het is a 5- or 6-membered heterocyclic ring containing one to three heteroatoms, each independently selected from oxygen, nitrogen and sulphur, the ring being substituted by one to three groups $R^4$; $R^1$ is hydrogen, optionally substituted $(C_{1-4})$alkyl, formyl, optionally substituted $(C_{1-4})$alkylC(=O), optionally substituted $(C_{1-4})$alkylC(=O)O, optionally substituted $(C_{1-4})$alkoxy$(C_{1-4})$alkyl, optionally substituted allyl, optionally substituted propargyl or optionally substituted allenyl; each $R^2$ is, independently, halogen, optionally substituted $(C_{1-4})$alkyl, optionally substituted $(C_{1-4})$alkoxy or optionally substituted $(C_{1-4})$alkoxy$(C_{1-4})$alkyl; $R^3$ is either at position 2 or at position 4 of the thiophene ring and is an organic group containing three to thirteen carbon atoms and at least one silicon atom and, optionally, one to three heteroatoms, each independently selected from oxygen, nitrogen and sulphur, and is optionally substituted by one to four independently selected halogen atoms; each $R^4$ is, independently, halogen, $C_{1-3}$ alkyl, $C_{1-3}$ haloalkyl, $C_{1-3}$alkoxy$(C_{1-3})$alkyl or cyano; r is 0, 1 or 2; and X is O or S; or an N-oxide thereof, to novel intermediates used in the preparation of these compounds, to agrochemical compositions which comprise at least one of the novel compounds as an active ingredient and to the use of the active ingredients or compositions in agriculture or horticulture for controlling or preventing infestation of plants by phytopathogenic microorganisms, preferably fungi.

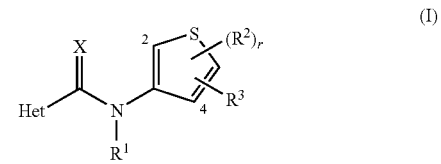

7 Claims, No Drawings

3-CARBONYLAMINOTHIOPHENES AND THEIR USE AS FUNGICIDES

This application is a 371 of International Application No. PCT/EP2004/004194 filed Apr. 21, 2004, which claims the benefit of Application No. GB0310464.3 filed May 7, 2003, Application No. GB0318920.6 filed Aug. 12, 2003, and Application No. GB0404806.2 filed Mar. 3, 2004, the respective contents of which are each incorporated herein by reference.

The present invention relates to novel thiophene-3-amides, substituted in the 2- or 4-position of the thiophene ring by a silicon containing substituent, which have microbiocidal activity, in particular fungicidal activity. The invention also relates to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

Certain thiophene amides, substituted by a silicon containing substituent, are disclosed in U.S. Pat. No. 5,739,338 and WO 97/19062.

The present invention provides a compound of formula (I)

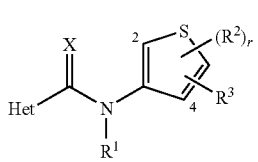

where Het is a 5- or 6-membered heterocyclic ring containing one to three heteroatoms, each independently selected from oxygen, nitrogen and sulphur, the ring being substituted by one to three groups $R^4$; $R^1$ is hydrogen, optionally substituted $(C_{1-4})$alkyl, formyl, optionally substituted $(C_{1-4})$alkylC(=O), optionally substituted $(C_{1-4})$alkylC(=O)O, optionally substituted $(C_{1-4})$alkoxy$(C_{1-4})$alkyl, optionally substituted allyl, optionally substituted propargyl or optionally substituted allenyl; each $R^2$ is, independently, halogen, optionally substituted $(C_{1-4})$alkyl, optionally substituted $(C_{1-4})$alkoxy or optionally substituted $(C_{1-4})$alkoxy$(C_{1-4})$alkyl;

$R^3$ is either at position 2 or at position 4 of the thiophene ring and is an organic group containing three to thirteen carbon atoms and at least one silicon atom and, optionally, one to three heteroatoms, each independently selected from oxygen, nitrogen and sulphur, and is optionally substituted by one to four independently selected halogen atoms; each $R^4$ is, independently, halogen, $C_{1-3}$ allyl, $C_{1-3}$ haloalkyl, $C_{1-3}$alkoxy$(C_{1-3})$alkyl or cyano; r is 0, 1 or 2; and X is O or S; or an N-oxide thereof.

In another aspect the present invention provides a compound of formula (I) as defined above provided that the Het ring is not 1,2,3-triazole when X is O.

Halogen is fluorine, chlorine, bromine or iodine, preferably fluorine, chlorine or bromine.

Each alkyl moiety is a straight or branched chain and is, for example, methyl, ethyl, n-propyl, n-butyl, iso-propyl, n-butyl, sec-butyl, iso-butyl or tert-butyl.

The alkenyl moieties, where appropriate, can be of either the (E)- or (Z)-configuration.

When present, each optional substituent on alkyl moieties, allyl, propargyl and allenyl is, independently, selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy and trifluorothiomethoxy.

Preferably $R^1$ is hydrogen, propargyl, allenyl, formyl, $CH_3C(=O)$, $C_2H_5C(=O)$ or $CH_3OCH_2C(=O)$.

More preferably $R^1$ is hydrogen, propargyl, allenyl, $CH_3C(=O)$, $C_2H_5C(=O)$ or $CH_3OCH_2C(=O)$.

Most preferably $R^1$ is hydrogen.

Preferably, each $R^2$ is independently selected from halogen, methyl, trifluoromethyl and trifluoromethoxy.

It is preferred that Het is pyrazolyl, pyrrolyl, thiophenyl, furyl, thiazolyl, isothiazolyl, oxazolyl, isoxazolyl, triazolyl, pyridinyl, pyrazinyl, pyrimidinyl, pyridazinyl, 5.6-dihydropyranyl or 5.6-dihydro-1.4-oxathiinyl (more preferably pyrazolyl, pyrrolyl, thiophenyl, furyl, thiazolyl, oxazolyl, 1,2,3-triazolyl, pyridinyl, pyrimidinyl, pyridazinyl, 5.6-dihydropyranyl or 5.6-dihydro-1.4-oxathiinyl) each being substituted by one to three groups $R^4$.

Preferably $R^3$ is an aliphatic, saturated or unsaturated group containing three to thirteen carbon atoms and at least one silicon atom and, optionally, one to three heteroatoms, each independently selected from oxygen, nitrogen and sulphur, and is optionally substituted by one to four independently selected halogen atoms.

More preferably $R^3$ is $Y^1$—$Si(O_mMe)(O_nMe)(O_pY^2)$ where m, n and p are each, independently, 0 or 1; $Y^1$ is a bond or is alkandiyl (alkylene), alkendiyl (alkenylene) or alkindiyl (alkynylene), each of which is branched or unbranched and contains 1-6 carbon atoms optionally interrupted by one or two oxygen atoms and optionally substituted by one to three independently selected halogen atoms; and $Y^2$ is alkyl or alkenyl, each of which is branched or unbranched and contains 1-5 carbon atoms optionally interrupted by one heteroatom selected from O, S and N and optionally substituted by one to three independently selected halogen atoms.

Even more preferably $R^3$ is $SiMe_3$, $SiMe_2Et$, $SiMe_2CHMe_2$, $SiMe_2CH_2CHMe_2$, $SiMe_2CH_2CMe_3$, $SiMe_2OCHMe_2$, $SiMe_2OCH_2CHMe_2$, $CH_2SiMe_3$, $CH_2Me_2Et$, $CH_2SiMe_2CHMe_2$, $CH_2SiMe_2CH_2CHMe_2$, $CH_2SiMe_2OMe$, $CH_2SiMe_2OCHMe_2$, $CH_2SiMe_2OCH_2CHMe_2$, $CHMeSiMe_3$, $CHMeSiMe_2OMe$, $(CH_2)_2SiMe_3$, $(CH_2)_2SiMe_2Et$, $(CH_2)_2SiMe_2CHMe_2$, $(CH_2)_2 SiMe_2CMe_3$, $(CH_2)_2SiMe_2CH_2CHMe_2$, $(CH_2)_2 SiMe_2CH_2CH_2Me$, $(CH_2)_2SiMe_2CH_2CMe_3$, $(CH_2)_2 SiMe_2OCHMe_2$, $(CH_2)_2SiMe_2OCH_2CHMe_2$, $CHMeCH_2SiMe_3$, $CHMeCH_2SiMe_2Et$, $CHMeCH_2SiMe_2CH_2CH_2Me$, $CHMeCH_2SiMe_2CHMe_2$, $CHMeCH_2SiMe_2CMe_3$, $CHMeCH_2SiMe_2CH_2CHMe_2$, $CFMeCH_2SiMe_3$, $CHMeCH_2CH_2SiMe_2OMe$, $CHMeCH_2SiMe_2OCHMe_2$, $CHMeCH_2SiMe_2OCH_2CHMe_2$, $CH_2CHMeSiMe_3$, $CH_2CHMeSiMe_2Et$, $CH_2CHMeSiMe_2CHMe_2$, $CHMeCH-MeSiMe_3$, $CMe_2CH_2SiMe_3$, $(CH_2)_3SiMe_3$, $(CH_2)_3SiMe_2Et$, $(CH_2)_3SiMe_2CHMe_2$, $(CH_2)_3SiMe_2CH_2CHMe_2$, $(CH_2)_3 SiMe_2OMe$, $(CH_2)_3SiMe_2OCHMe_2$, $(CH_2)_3 SiMe_2OCH_2CHMe_2$, $CHMeCH_2CH_2SiMe_3$, $CHMeCH_2CH_2SiMe_2Et$, $CHMeCH_2CH_2SiMe_2CHMe_2$, $CHMeCH_2CH_2CH_2SiMe_2OMe$, $CHMeCH_2CH_2SiMe_2OCHMe_2$, $CMe=CHSiMe_3$ or $CH_2CH_2SiMe_2OMe$.

Most preferably $R^3$ is $SiMe_3$, $SiMe_2Et$, $SiMe_2CHMe_2$, $SiMe_2CH_2CHMe_2$, $SiMe_2CH_2CMe_3$, $(CH_2)_2SiMe_3$, $(CH_2)_2$ SiMe$_2$Et, (CH$_2$)$_2$SiMe$_2$CHMe$_2$, (CH$_2$)$_2$SiMe$_2$CMe$_3$, (CH$_2$)$_2$SiMe$_2$CH$_2$CHMe$_2$, CHMeCH$_2$SiMe$_3$, CHMeCH$_2$SiMe$_2$Et, CH$_2$CHMeSiMe$_3$, CMe$_2$CH$_2$SiMe$_3$ or (CH$_2$)$_3$SiMe$_3$.

Nitrogen atoms in the Het ring are, independently, either unsubstituted or substituted by R$^4$. When R$^4$ is a substituent on a nitrogen atom it is preferably C$_{1-3}$ alkyl, C$_{1-3}$ haloalkyl or methoxymethylene; more preferably C$_{1-2}$ alkyl, CF$_3$, CF$_2$Cl, CHF$_2$, CH$_2$F or methoxymethylene; even more preferably methyl, CHF$_2$ or methoxymethylene; yet more preferably methyl or methoxymethylene; and most preferably methyl.

Carbon atoms in the Het ring which are not bonded to the atom substituted by CXNR$^1$ are, independently, either unsubstituted or substituted by R$^4$. When R$^4$ is a substituent on a carbon atom which is not bonded to the atom substituted by CXNR$^1$ it is preferably halogen, C$_{1-3}$ alkyl, C$_{1-3}$ haloalkyl or methoxymethylene; more preferably chloro, methoxymethylene, CH$_3$, CHF$_2$ or CF$_3$; yet more preferably chloro, CH$_3$, CHF$_2$ or CF$_3$; and even more preferably CH$_3$ or CF$_3$.

There may be one or two carbon atoms in the Het ring bonded to the atom substituted by CXNR$^1$; such carbon atoms are, independently, either unsubstituted or substituted by R$^4$. When R$^4$ is a substituent on a carbon atom bonded to the atom substituted by CXNR$^1$ it is preferably halogen, C$_{1-3}$ alkyl or C$_{1-3}$ haloalkyl; more preferably chloro, fluoro, bromo, C$_{1-2}$ alkyl, CF$_3$, CF$_2$Cl, CHF$_2$ or CH$_2$F; and even more preferably chloro, fluoro, bromo, methyl, CF$_3$, CHF$_2$ or CH$_2$F.

More preferably, when there is only one carbon atom in the Het ring bonded to the atom substituted by CXNR$^1$ that carbon atom is substituted by R$^4$.

More preferably, when there are two carbon atoms in the Het ring bonded to the atom substituted by CXNR$^1$ one such carbon atom is substituted by R$^4$ and the other carbon atom is either unsubstituted or is substituted by fluoro, chloro or methyl.

Most preferably the combination of Het, R$^4$ and CXNR$^1$ is 1-Me-3-R$^4$-4-CXNR$^1$ pyrazolyl, 1-Me-3-R$^4$-4-CXNR$^1$ pyrrolyl, 2-Me-3-R$^4$-4-CXNR$^1$ thiazoyl or 2-R$^4$-3-CXNR$^1$ pyridinyl.

Preferably X is oxygen.

Preferably r is 0.

When a compound of formula (I) is an N-oxide then it is preferred that Het is pyridinyl substituted by one to three groups R$^4$.

Throughout this description, Me is used to represent the methyl group. Likewise, Et represents the ethyl group.

Thiophenes of formulae (IIa) and (IIb)

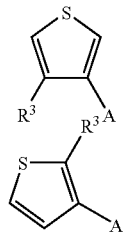

where R$^3$ is as defined above and A is NH$_2$, NHCH(O), optionally substituted C$_{1-4}$alkylC(=O)NH, optionally substituted (C$_{1-4}$)alkylOC(=O)NH, halogen or N=C(C$_6$H$_5$)$_2$ are useful as intermediates in the preparation of compounds of formula (I).

Compounds of formulae (IIa) and (IIb) where R$^3$ is SiMe$_2$Et, SiMe$_2$CHMe$_2$, SiMe$_2$CH$_2$CHMe$_2$, SiMe$_2$CH$_2$CMe$_3$, CH=CHSiMe$_3$, (CH$_2$)$_2$SiMe$_3$, (CH$_2$)$_2$SiMe$_2$Et, (CH$_2$)$_2$SiMe$_2$CHMe$_2$, (CH$_2$)$_2$SiMe$_2$CMe$_3$, (CH$_2$)$_2$SiMe$_2$CH$_2$CHMe$_2$, CHMeCH$_2$SiMe$_3$, CHMeCH$_2$SiMe$_2$Et, CH$_2$CHMeSiMe$_3$, CMe$_2$CH$_2$SiMe$_3$ or (CH$_2$)$_3$SiMe$_3$; and A is as defined above [provided that A is not halogen when R$^3$ is SiMe3] are novel and are preferred as intermediates for the preparation of compounds of formula (I). Compounds of formulae (IIa) and (IIb) where R$^3$ is SiMe$_3$ and A is halogen are already known.

Therefore, in another aspect the present invention provides a compound of formula (IIa) or (IIb) where R$^3$ is SiMe$_3$, SiMe$_2$Et, SiMe$_2$CHMe$_2$, SiMe$_2$CH$_2$CHMe$_2$, SiMe$_2$CH$_2$CMe$_3$, CH=CHSiMe$_3$, (CH$_2$)$_2$SiMe$_3$, (CH$_2$)$_2$SiMe$_2$Et, (CH$_2$)$_2$SiMe$_2$CHMe$_2$, (CH$_2$)$_2$SiMe$_2$CMe$_3$, (CH$_2$)$_2$SiMe$_2$CH$_2$CHMe$_2$, CHMeCH$_2$SiMe$_3$, CHMeCH$_2$SiMe$_2$Et, CH$_2$CHMeSiMe$_3$, CMe$_2$CH$_2$SiMe$_3$, (CH$_2$)$_3$SiMe$_3$; and A is NH$_2$, NHCH(O), optionally substituted (C$_{1-4}$)alkylC(=O)NH, optionally substituted (C$_{1-4}$)alkylOC(=O)NH, halogen or N=C(C$_6$H$_5$)$_2$; provided that A is not halogen when R$^3$ is SiMe$_3$.

The compounds of formula (I), (IIa) and (IIb) may exist as different geometric or optical isomers or in different tautomeric forms. This invention covers all such isomers and tautomers and mixtures thereof in all proportions as well as isotopic forms such as deuterated compounds.

The compounds in Tables 1 to 28 below illustrate particularly preferred compounds of the invention, in which R$^5$, R$^6$ and R$^7$ are each, independently, examples of R$^4$ as defined above.

Table A represents Table 1 (when A is 1), represents Table 2 (when A is 2), represents Table 3 (when A is 3) and represents Table 4 (when A is 4).

TABLE A

| Compound No. | R$^1$ | R$^3$ | R$^5$ | R$^6$ | R$^7$ | X |
|---|---|---|---|---|---|---|
| A.1 | H | SiMe$_3$ | H | Me | CF$_3$ | O |
| A.2 | H | SiMe$_3$ | H | Me | CF$_2$H | O |
| A.3 | H | CH$_2$SiMe$_3$ | H | Me | CF$_3$ | O |
| A.4 | H | CH$_2$SiMe$_3$ | H | Me | CF$_3$ | S |
| A.5 | H | CH$_2$SiMe$_3$ | H | Me | CF$_2$H | O |
| A.6 | propargyl | CH$_2$SiMe$_3$ | H | Me | CF$_3$ | O |
| A.7 | H | CHMeSiMe$_3$ | H | Me | CF$_3$ | O |
| A.8 | H | CHMeSiMe$_3$ | H | Me | CF$_2$H | O |

TABLE A-continued

| Compound No. | R$^1$ | R$^3$ | R$^5$ | R$^6$ | R$^7$ | X |
|---|---|---|---|---|---|---|
| A.9 | H | CHMeSiMe$_3$ | H | Me | CF$_3$ | S |
| A.10 | propargyl | CHMeSiMe$_3$ | H | Me | CF$_3$ | O |
| A.11 | allenyl | CHMeSiMe$_3$ | H | Me | CF$_3$ | O |
| A.12 | COMe | CHMeSiMe$_3$ | H | Me | CF$_3$ | O |
| A.13 | H | CHMeSiMe$_3$ | F | Me | Me | O |
| A.14 | H | (CH$_2$)$_2$SiMe$_3$ | H | Me | CF$_3$ | O |
| A.15 | H | (CH$_2$)$_2$SiMe$_3$ | H | Me | CF$_3$ | S |
| A.16 | H | (CH$_2$)$_2$SiMe$_3$ | H | Me | CF$_2$H | O |
| A.17 | propargyl | (CH$_2$)$_2$SiMe$_3$ | H | Me | CF$_3$ | O |
| A.18 | H | (CH$_2$)$_2$SiMe$_3$ | F | Me | Me | O |
| A.19 | H | (CH$_2$)$_2$SiMe$_3$ | H | CH$_2$OMe | CF$_3$ | O |
| A.20 | H | (CH$_2$)$_2$SiMe$_3$ | H | CH$_2$OMe | CF$_2$H | O |
| A.21 | H | CHMeCH$_2$SiMe$_3$ | H | Me | CF$_3$ | O |
| A.22 | H | CHMeCH$_2$SiMe$_3$ | H | Me | CF$_3$ | S |
| A.23 | H | CHMeCH$_2$SiMe$_3$ | H | CH$_2$OMe | CF$_3$ | O |
| A.24 | H | CHMeCH$_2$SiMe$_3$ | H | Me | CF$_2$H | O |
| A.25 | H | CHMeCH$_2$SiMe$_3$ | H | Me | CF$_2$H | S |
| A.26 | propargyl | CHMeCH$_2$SiMe$_3$ | H | Me | CF$_3$ | O |
| A.27 | allenyl | CHMeCH$_2$SiMe$_3$ | H | Me | CF$_3$ | O |
| A.28 | propargyl | CHMeCH$_2$SiMe$_3$ | H | Me | CF$_2$H | O |
| A.29 | allenyl | CHMeCH$_2$SiMe$_3$ | H | Me | CF$_2$H | O |
| A.30 | H | CHMeCH$_2$SiMe$_3$ | F | Me | Me | O |
| A.31 | COMe | CHMeCH$_2$SiMe$_3$ | H | Me | CF$_3$ | O |
| A.32 | H | (CH$_2$)$_3$SiMe$_3$ | H | Me | CF$_2$H | O |
| A.33 | H | CH$_2$Si(Me$_2$)Et | H | Me | CF$_3$ | O |
| A.34 | H | CH$_2$Si(Me$_2$)Et | H | Me | CF$_2$H | O |
| A.35 | H | CH$_2$Si(Me$_2$)CHMe$_2$ | H | Me | CF$_3$ | O |
| A.36 | H | CH$_2$Si(Me$_2$)CHMe$_2$ | H | Me | CF$_2$H | O |
| A.37 | H | CH$_2$Si(Me$_2$)OMe | H | Me | CF$_3$ | O |
| A.38 | H | CH$_2$Si(Me$_2$)OMe | H | Me | CF$_2$H | O |
| A.39 | H | CH$_2$CH$_2$Si(Me$_2$)OMe | H | Me | CF$_3$ | O |
| A.40 | H | CHMeSi(Me$_2$)OMe | H | Me | CF$_3$ | O |
| A.41 | H | CHMeSi(Me$_2$)OMe | H | Me | CF$_2$H | O |
| A.42 | H | CH$_2$CH$_2$Si(Me$_2$)OMe | H | Me | CF$_2$H | O |
| A.43 | H | C(Me)=CHSiMe$_3$ | H | Me | CF$_3$ | O |
| A.44 | H | SiMe$_3$ | H | Me | CH$_2$F | O |
| A.45 | H | (CH$_2$)$_2$SiMe$_3$ | H | Me | CH$_2$F | O |
| A.46 | H | CH$_2$CHMeSiMe$_3$ | H | Me | CH$_2$F | O |
| A.47 | H | CH$_2$CHMeSiMe$_3$ | H | Me | CF$_3$ | O |
| A.48 | H | CH$_2$CHMeSiMe$_3$ | H | Me | CF$_2$H | O |
| A.49 | H | CHMeCH$_2$SiMe$_3$ | H | Me | CH$_2$F | O |
| A.50 | H | CMe$_2$CH$_2$SiMe$_3$ | H | Me | CF$_3$ | O |
| A.51 | H | CMe$_2$CH$_2$SiMe$_3$ | H | Me | CF$_2$H | O |
| A.52 | H | CHMeCHMeSiMe$_3$ | H | Me | CF$_2$H | O |
| A.53 | H | CHMeCHMeSiMe$_3$ | H | Me | CF$_3$ | O |
| A.54 | H | CH$_2$CMe$_2$SiMe$_3$ | H | Me | CF$_3$ | O |
| A.55 | H | CH$_2$CMe$_2$SiMe$_3$ | H | Me | CF$_2$H | O |
| A.56 | H | CHMe(CH$_2$)$_2$SiMe$_3$ | H | Me | CF$_2$H | O |
| A.57 | H | CHMe(CH$_2$)$_2$SiMe$_3$ | H | Me | CF$_3$ | O |
| A.58 | H | (CH$_2$)$_2$Si(Me$_2$)(CH$_2$)$_2$Me | H | Me | CF$_2$H | O |
| A.59 | H | (CH$_2$)$_2$Si(Me$_2$)(CH$_2$)$_2$Me | H | Me | CF$_3$ | O |
| A.60 | H | CHMeCH$_2$Si(Me$_2$)CMe$_3$ | H | Me | CF$_3$ | O |
| A.61 | H | C(=CH$_2$)CH$_2$Si(Me$_2$)CMe$_3$ | H | Me | CF$_3$ | O |
| A.62 | H | C(=CH$_2$)CH$_2$Si(Me$_2$)CH$_2$Me | H | Me | CF$_3$ | O |
| A.63 | H | (CH$_2$)$_2$Si(Me$_2$)CH$_2$Me | H | Me | CF$_3$ | O |
| A.64 | H | CHMeCH$_2$Si(Me$_2$)CH$_2$Me | H | Me | CF$_3$ | O |
| A.65 | H | (CH$_2$)$_2$Si(Me$_2$)CHMe$_2$ | H | Me | CF$_3$ | O |
| A.66 | H | CHMeCH$_2$Si(Me$_2$)CHMe$_2$ | H | Me | CF$_3$ | O |
| A.67 | H | CHMeCH$_2$Si(Me$_2$)CH$_2$CHMe$_2$ | H | Me | CF$_3$ | O |
| A.68 | H | Si(Me$_2$)CH$_2$Me | H | Me | CF$_2$H | O |
| A.69 | H | Si(Me$_2$)CH$_2$Me | H | Me | CF$_3$ | O |
| A.70 | H | Si(Me$_2$)CHMe$_2$ | H | Me | CF$_3$ | O |
| A.71 | H | Si(Me$_2$)CHMe$_2$ | H | Me | CF$_2$H | O |
| A.72 | H | Si(Me$_2$)CH$_2$CHMe$_2$ | H | Me | CF$_2$H | O |
| A.73 | H | Si(Me$_2$)CH$_2$CHMe$_2$ | H | Me | CF$_3$ | O |
| A.74 | H | C:CCH$_2$SiMe$_3$ | H | Me | CF$_3$ | O |
| A.75 | propargyl | (CH$_2$)$_2$SiMe$_3$ | H | Me | CF$_2$H | O |
| A.76 | allenyl | (CH$_2$)$_2$SiMe$_3$ | H | Me | CF$_2$H | O |
| A.77 | allenyl | (CH$_2$)$_2$SiMe$_3$ | H | Me | CF$_3$ | O |
| A.78 | H | (CH$_2$)$_2$SiMe$_3$ | H | Me | CF$_2$Cl | O |
| A.79 | H | (CH$_2$)$_3$SiMe$_3$ | H | Me | CF$_3$ | O |
| A.80 | H | (CH$_2$)$_2$SiMe$_3$ | Br | Me | CF$_3$ | O |
| A.81 | H | (CH$_2$)$_2$SiMe$_3$ | Cl | Me | CF$_3$ | O |
| A.82 | H | (CH$_2$)$_2$SiMe$_3$ | H | Me | Me | O |
| A.83 | H | C:CSiMe$_3$ | H | Me | CF$_3$ | O |
| A.84 | H | C:CSiMe$_3$ | H | Me | CF$_2$H | O |

TABLE A-continued

| Compound No. | R¹ | R³ | R⁵ | R⁶ | R⁷ | X |
|---|---|---|---|---|---|---|
| A.85 | CHO | (CH₂)₂SiMe₃ | H | Me | CF₂H | O |
| A.86 | CHO | (CH₂)₂SiMe₃ | H | Me | CF₃ | O |

Table 1 provides 86 compounds of formula (Ia) where $R^1$, $R^3$, $R^5$, $R^6$, $R^7$ and X are as defined in Table 1.

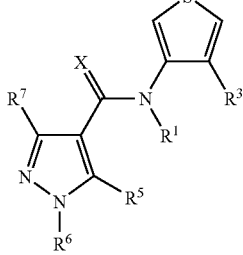

(Ia)

Table 2 provides 86 compounds of formula (Ib) where $R^1$, $R^3$, $R^5$, $R^6$, $R^7$ and X are as defined in Table 2.

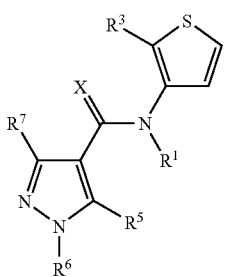

(Ib)

Table 3 provides 86 compounds of formula (Ic) where $R^1$, $R^3$, $R^5$, $R^6$, $R^7$ and X are as defined in Table 3.

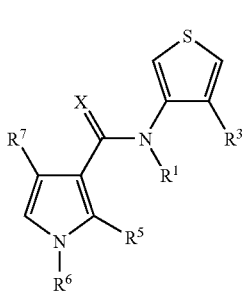

(Ic)

Table 4 provides 86 compounds of formula (Id) where $R^1$, $R^3$, $R^5$, $R^6$, $R^7$ and X are as defined in Table 4.

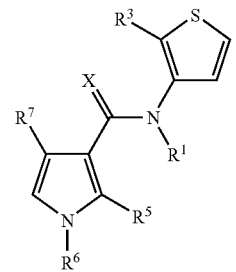

(Id)

Table B represents Table 5 (when B is 5), represents Table 6 (when B is 6), represents Table 7 (when B is 7) and represents Table 8 (when B is 8).

TABLE B

| Compound No. | R¹ | R³ | R⁵ | R⁶ | X |
|---|---|---|---|---|---|
| B.1 | H | SiMe₃ | Me | CF₃ | O |
| B.2 | H | SiMe₃ | Me | CF₂H | O |
| B.3 | H | CH₂SiMe₃ | Me | CF₃ | O |
| B.4 | H | CH₂SiMe₃ | Me | CF₃ | S |
| B.5 | H | CH₂SiMe₃ | Me | CF₂H | O |
| B.6 | propargyl | CH₂SiMe₃ | Me | CF₃ | O |
| B.7 | H | CHMeSiMe₃ | Me | CF₃ | O |
| B.8 | H | CHMeSiMe₃ | Me | CF₂H | O |
| B.9 | H | CHMeSiMe₃ | Me | CF₃ | S |
| B.10 | propargyl | CHMeSiMe₃ | Me | CF₃ | O |
| B.11 | allenyl | CHMeSiMe₃ | Me | CF₃ | O |
| B.12 | COMe | CHMeSiMe₃ | Me | CF₃ | O |
| B.13 | H | CHMeSiMe₃ | Me | Me | O |
| B.14 | H | (CH₂)₂SiMe₃ | Me | CF₃ | O |
| B.15 | H | (CH₂)₂SiMe₃ | Me | CF₃ | S |
| B.16 | H | (CH₂)₂SiMe₃ | Me | CF₂H | O |
| B.17 | propargyl | (CH₂)₂SiMe₃ | Me | CF₃ | O |
| B.18 | H | (CH₂)₂SiMe₃ | Me | Me | O |
| B.19 | H | (CH₂)₂SiMe₃ | CF₃ | CF₃ | O |
| B.20 | H | CHMeCH₂SiMe₃ | Me | CF₃ | O |
| B.21 | H | CHMeCH₂SiMe₃ | Me | CF₃ | S |
| B.22 | H | CHMeCH₂SiMe₃ | Me | CF₂H | O |
| B.23 | H | CHMeCH₂SiMe₃ | Me | CF₂H | S |
| B.24 | propargyl | CHMeCH₂SiMe₃ | Me | CF₃ | O |
| B.25 | propargyl | CHMeCH₂SiMe₃ | Me | CF₂H | O |
| B.26 | H | CHMeCH₂SiMe₃ | Me | Me | O |
| B.27 | H | CHMeCH₂SiMe₃ | CF₃ | CF₃ | O |
| B.28 | COMe | CHMeCH₂SiMe₃ | Me | CF₃ | O |
| B.29 | H | (CH₂)₃SiMe₃ | Me | CF₃ | O |
| B.30 | H | (CH₂)₃SiMe₃ | Me | CF₂H | O |
| B.31 | H | CH₂Si(Me₂)Et | Me | CF₃ | O |
| B.32 | H | CH₂Si(Me₂)Et | Me | CF₂H | O |
| B.33 | H | CH₂Si(Me₂)CHMe₂ | Me | CF₃ | O |
| B.34 | H | CH₂Si(Me₂)CHMe₂ | Me | CF₂H | O |
| B.35 | H | CH₂CHMeSiMe₃ | Me | CF₃ | O |
| B.36 | H | CH₂CHMeSiMe₃ | Me | CF₂H | O |
| B.37 | H | CMe₂CH₂SiMe₃ | Me | CF₃ | O |
| B.38 | H | CMe₂CH₂SiMe₃ | Me | CF₂H | O |
| B.39 | H | CHMeCHMeSiMe₃ | Me | CF₂H | O |
| B.40 | H | CHMeCHMeSiMe₃ | Me | CF₃ | O |
| B.41 | H | CH₂CMe₂SiMe₃ | Me | CF₃ | O |
| B.42 | H | CH₂CMe₂SiMe₃ | Me | CF₂H | O |

TABLE B-continued

| Compound No. | R¹ | R³ | R⁵ | R⁶ | X |
|---|---|---|---|---|---|
| B.43 | H | $CHMe(CH_2)_2SiMe_3$ | Me | $CF_2H$ | O |
| B.44 | H | $CHMe(CH_2)_2SiMe_3$ | Me | $CF_3$ | O |
| B.45 | H | $(CH_2)_2SiMe_3$ | $CH_2OMe$ | $CH_2Me$ | O |
| B.46 | H | $(CH_2)_2SiMe_3$ | $CH_2OCH_2Me$ | $CH_2Me$ | O |
| B.47 | H | $SiMe_2CH_2CHMe_2$ | Me | $CF_3$ | O |

Table 5 provides 47 compounds of formula (Ie) where $R^1$, $R^3$, $R^5$, $R^6$ and X are as defined in Table 5.

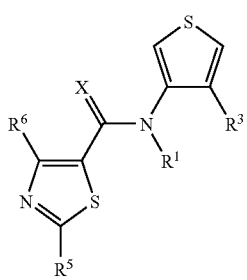
(Ie)

Table 6 provides 47 compounds of formula (If) where $R^1$, $R^3$, $R^5$, $R^6$ and X are as defined in Table 6.

(If)

Table 7 provides 47 compounds of formula (Ig) where $R^1$, $R^3$, $R^5$, $R^6$ and X are as defined in Table 7.

(Ig)

Table 8 provides 47 compounds of formula (Ih) where $R^1$, $R^3$, $R^5$, $R^6$ and X are as defined in Table 8.

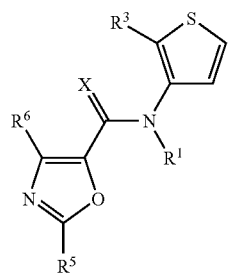
(Ih)

Table BB represents Table 9 (when BB is 9) and represents Table 10 (when BB is 10).

TABLE BB

| Compound No. | R¹ | R³ | R⁵ | R⁶ | X |
|---|---|---|---|---|---|
| BB.1 | H | $CH_2SiMe_3$ | Me | $CF_3$ | S |
| BB.2 | H | $CHMeSiMe_3$ | Me | $CF_3$ | S |
| BB.3 | H | $(CH_2)_2SiMe_3$ | Me | $CF_3$ | S |
| BB.4 | H | $CHMeCH_2SiMe_3$ | Me | $CF_3$ | S |
| BB.5 | H | $CHMeCH_2SiMe_3$ | Me | $CF_2H$ | S |

Table 9 provides 5 compounds of formula (Ii) where $R^1$, $R^3$, $R^5$, $R^6$ and X are as defined in Table 9.

(Ii)

Table 10 provides 5 compounds of formula (Ij) where $R^1$, $R^3$, $R^5$, $R^6$ and X are as defined in Table 10.

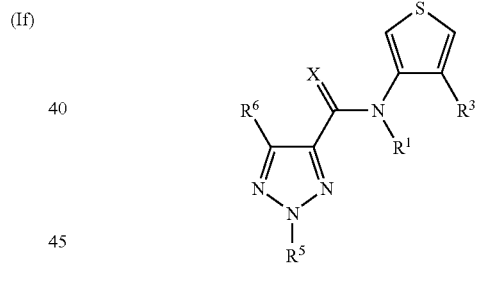
(Ij)

Table C represents Table 11 (when C is 11), represents Table 12 (when C is 12), represents Table 13 (when C is 13) and represents Table 14 (when C is 14).

TABLE C

| Compound No. | R¹ | R³ | R⁵ | R⁶ | R⁷ | X |
|---|---|---|---|---|---|---|
| C.1 | H | SiMe₃ | Me | Me | H | O |
| C.2 | H | SiMe₃ | Me | Me | H | O |
| C.3 | H | CH₂SiMe₃ | Me | Me | Me | O |
| C.4 | H | CH₂SiMe₃ | Me | Me | CF₃ | O |
| C.5 | H | CH₂SiMe₃ | Me | Me | H | O |
| C.6 | propargyl | CH₂SiMe₃ | Me | Me | CF₃ | O |
| C.7 | H | CHMeSiMe₃ | Me | Me | CF₃ | O |
| C.8 | H | CHMeSiMe₃ | Me | Me | Me | O |
| C.9 | H | CHMeSiMe₃ | Me | Me | Me | S |
| C.10 | propargyl | CHMeSiMe₃ | Me | Me | Me | O |
| C.11 | allenyl | CHMeSiMe₃ | Me | Me | Me | O |
| C.12 | COMe | CHMeSiMe₃ | Me | Me | Me | O |
| C.13 | H | CHMeSiMe₃ | Me | Me | Me | O |
| C.14 | H | (CH₂)₂SiMe₃ | Me | Me | CF₃ | O |
| C.15 | H | (CH₂)₂SiMe₃ | H | H | CF₃ | O |
| C.16 | H | (CH₂)₂SiMe₃ | H | H | CF₃ | S |
| C.17 | propargyl | (CH₂)₂SiMe₃ | H | H | CF₃ | O |
| C.18 | H | (CH₂)₂SiMe₃ | Me | Me | H | O |
| C.19 | H | CHMeCH₂SiMe₃ | H | H | CF₃ | O |
| C.20 | H | CHMeCH₂SiMe₃ | H | H | CF₃ | S |
| C.21 | H | CHMeCH₂SiMe₃ | Me | Me | Me | O |
| C.22 | H | CHMeCH₂SiMe₃ | H | Me | CF₃ | O |
| C.23 | H | CHMeCH₂SiMe₃ | Me | Me | H | O |
| C.24 | COMe | CHMeCH₂SiMe₃ | Me | Me | H | O |
| C.25 | propargyl | CHMeCH₂SiMe₃ | Me | Me | H | O |
| C.26 | allenyl | CHMeCH₂SiMe₃ | Me | Me | H | O |
| C.27 | propargyl | CHMeCH₂SiMe₃ | Me | Me | Me | O |
| C.28 | allenyl | CHMeCH₂SiMe₃ | Me | Me | Me | O |
| C.29 | COMe | CHMeCH₂SiMe₃ | Me | Me | Me | O |
| C.30 | COEt | CHMeCH₂SiMe₃ | Me | Me | Me | O |
| C.31 | H | CH₂CHMeSiMe₃ | H | H | CF₃ | O |
| C.32 | H | CH₂CHMeSiMe₃ | H | H | CF₃ | S |
| C.33 | H | CH₂CHMeSiMe₃ | Me | Me | Me | O |
| C.34 | H | CH₂CHMeSiMe₃ | H | Me | CF₃ | O |
| C.35 | H | CH₂CHMeSiMe₃ | Me | Me | H | O |

Table 11 provides 35 compounds of formula (Ik) where $R^1$, $R^3$, $R^5$, $R^6$, $R^7$ and X are as defined in Table 11.

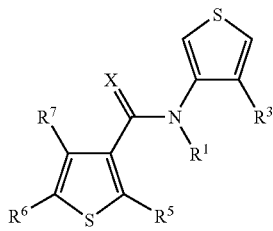

(Ik)

Table 12 provides 35 compounds of formula (Il) where $R^1$, $R^3$, $R^5$, $R^6$, $R^7$ and X are as defined in Table 12.

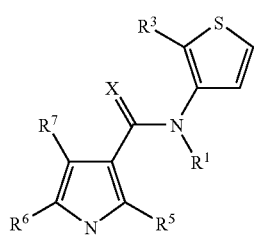

(Il)

Table 13 provides 35 compounds of formula (Im) where $R^1$, $R^3$, $R^5$, $R^6$, $R^7$ and X are as defined in Table 13.

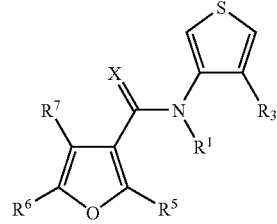

(Im)

Table 14 provides 35 compounds of formula (In) where $R^1$, $R^3$, $R^5$, $R^6$, $R^7$ and X are as defined in Table 14.

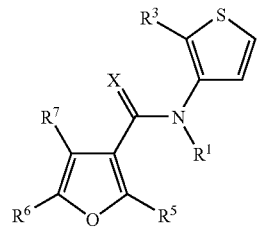

(In)

Table D represents Table 15 (when D is 15), represents Table 16 (when D is 16), represents Table 17 (when D is 17) and represents Table 18 (when D is 18).

TABLE D

| Compound No. | R¹ | R³ | R⁵ | X |
|---|---|---|---|---|
| D.1 | H | SiMe₃ | Me | O |
| D.2 | H | SiMe₃ | CF₃ | O |
| D.3 | H | CH₂SiMe₃ | Me | O |
| D.4 | H | CH₂SiMe₃ | CF₃ | S |
| D.5 | COMe | CH₂SiMe₃ | Me | O |
| D.6 | propargyl | CH₂SiMe₃ | Me | O |
| D.7 | H | CHMeSiMe₃ | Me | O |
| D.8 | H | CHMeSiMe₃ | CF₃ | O |
| D.9 | H | CHMeSiMe₃ | CF₃ | S |
| D.10 | propargyl | CHMeSiMe₃ | Me | O |
| D.11 | allenyl | CHMeSiMe₃ | Me | O |
| D.12 | COMe | CHMeSiMe₃ | Me | O |
| D.13 | propargyl | CHMeSiMe₃ | CF₃ | O |
| D.14 | H | (CH₂)₂SiMe₃ | Me | O |
| D.15 | H | (CH₂)₂SiMe₃ | CF₃ | O |
| D.16 | H | (CH₂)₂SiMe₃ | CF₃ | S |
| D.17 | propargyl | (CH₂)₂SiMe₃ | Me | O |
| D.18 | COMe | (CH₂)₂SiMe₃ | Me | O |
| D.19 | H | CHMeCH₂SiMe₃ | Me | O |
| D.20 | H | CHMeCH₂SiMe₃ | CF₃ | O |
| D.21 | H | CHMeCH₂SiMe₃ | CF₃ | S |
| D.22 | propargyl | CHMeCH₂SiMe₃ | Me | O |
| D.23 | allenyl | CHMeCH₂SiMe₃ | Me | O |
| D.24 | COMe | CHMeCH₂SiMe₃ | Me | O |
| D.25 | propargyl | CHMeCH₂SiMe₃ | CF₃ | O |
| D.26 | allenyl | CHMeCH₂SiMe₃ | CF₃ | O |
| D.27 | COMe | CHMeCH₂SiMe₃ | CF₃ | O |
| D.28 | allenyl | CHMeCH₂SiMe₃ | Me | O |
| D.29 | H | (CH₂)₃SiMe₃ | Me | O |
| D.30 | H | (CH₂)₃SiMe₃ | CF₃ | O |
| D.31 | H | CH₂CHMeSiMe₃ | Me | O |
| D.32 | H | CH₂CHMeSiMe₃ | CF₃ | O |

Table 15 provides 32 compounds of formula (Io) where $R^1$, $R^3$, $R^5$ and X are as defined in Table 15.

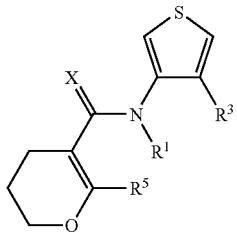

(Io)

Table 16 provides 32 compounds of formula (Ip) where $R^1$, $R^3$, $R^5$ and X are as defined in Table 16.

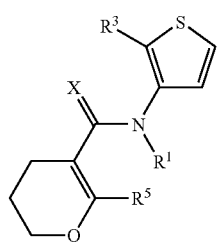

(Ip)

Table 17 provides 32 compounds of formula (Iq) where $R^1$, $R^3$, $R^5$ and X are as defined in Table 17.

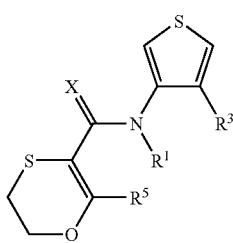

(Iq)

Table 18 provides 32 compounds of formula (Ir) where $R^1$, $R^3$, $R^5$ and X are as defined in Table 18.

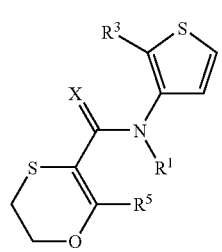

(Ir)

Table E represents Table 19 (when E is 19), represents Table 20 (when E is 20), represents Table 21 (when E is 21), represents Table 22 (when E is, 22), represents Table 23 (when E is 23) and represents Table 24 (when E is 24).

TABLE E

| Compound No. | $R^1$ | $R^3$ | $R^5$ | X |
|---|---|---|---|---|
| E.1 | H | SiMe$_3$ | Cl | O |
| E.2 | H | SiMe$_3$ | CF$_3$ | O |
| E.3 | H | CH$_2$SiMe$_3$ | Cl | O |
| E.4 | H | CH$_2$SiMe$_3$ | Br | O |
| E.5 | H | CH$_2$SiMe$_3$ | CF$_3$ | O |
| E.6 | propargyl | CH$_2$SiMe$_3$ | Cl | O |
| E.7 | H | CHMeSiMe$_3$ | Cl | O |
| E.8 | H | CHMeSiMe$_3$ | Br | O |
| E.9 | H | CHMeSiMe$_3$ | CF$_3$ | O |
| E.10 | propargyl | CHMeSiMe$_3$ | Cl | O |
| E.11 | allenyl | CHMeSiMe$_3$ | Cl | O |
| E.12 | COMe | CHMeSiMe$_3$ | Cl | O |
| E.13 | H | CHMeSiMe$_3$ | Cl | S |
| E.14 | H | (CH$_2$)$_2$SiMe$_3$ | Cl | O |
| E.15 | H | (CH$_2$)$_2$SiMe$_3$ | Br | O |
| E.16 | H | (CH$_2$)$_2$SiMe$_3$ | CF$_3$ | O |
| E.17 | propargyl | (CH$_2$)$_2$SiMe$_3$ | Cl | O |
| E.18 | COMe | (CH$_2$)$_2$SiMe$_3$ | Cl | O |
| E.19 | H | CHMeCH$_2$SiMe$_3$ | Cl | O |
| E.20 | H | CHMeCH$_2$SiMe$_3$ | Cl | S |
| E.21 | H | CHMeCH$_2$SiMe$_3$ | Br | O |
| E.22 | H | CHMeCH$_2$SiMe$_3$ | CF$_3$ | O |
| E.23 | propargyl | CHMeCH$_2$SiMe$_3$ | Cl | O |
| E.24 | allenyl | CHMeCH$_2$SiMe$_3$ | Cl | O |
| E.25 | COMe | CHMeCH$_2$SiMe$_3$ | Cl | O |
| E.26 | propargyl | CHMeCH$_2$SiMe$_3$ | Br | O |
| E.27 | allenyl | CHMeCH$_2$SiMe$_3$ | Br | O |
| E.28 | COMe | CHMeCH$_2$SiMe$_3$ | Br | O |
| E.29 | COCH$_2$OMe | CHMeCH$_2$SiMe$_3$ | Cl | O |
| E.30 | COCH$_2$OMe | CHMeCH$_2$SiMe$_3$ | CF$_3$ | O |
| E.31 | H | (CH$_2$)$_3$SiMe$_3$ | Cl | O |
| E.32 | H | (CH$_2$)$_3$SiMe$_3$ | Br | O |
| E.33 | H | (CH$_2$)$_3$SiMe$_3$ | CF$_3$ | O |
| E.34 | H | CH$_2$CHMeSiMe$_3$ | CF$_3$ | O |
| E.35 | H | CH$_2$CHMeSiMe$_3$ | Cl | O |
| E.36 | H | CH$_2$CHMeSiMe$_3$ | Br | O |
| E.37 | H | SiMe$_2$CH$_2$Me | CF$_3$ | O |
| E.38 | H | SiMe$_2$CH$_2$Me | Cl | O |
| E.39 | H | SiMe$_2$CH$_2$Me | Br | O |
| E.40 | H | SiMe$_2$CHMe$_2$ | CF$_3$ | O |
| E.41 | H | SiMe$_2$CHMe$_2$ | Cl | O |
| E.42 | H | SiMe$_2$CHMe$_2$ | Br | O |
| E.43 | H | SiMe$_2$CH$_2$CH$_2$Me | CF$_3$ | O |
| E.44 | H | SiMe$_2$CH$_2$CH$_2$Me | Cl | O |
| E.45 | H | SiMe$_2$CH$_2$CH$_2$Me | Br | O |

Table 19 provides 45 compounds of formula (Is) where $R^1$, $R^3$, $R^5$ and X are as defined in Table 19.

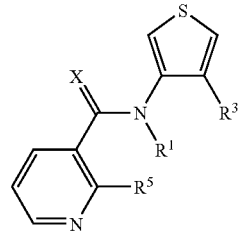

(Is)

Table 20 provides 45 compounds of formula (It) where $R^1$, $R^3$, $R^5$ and X are as defined in Table 20.

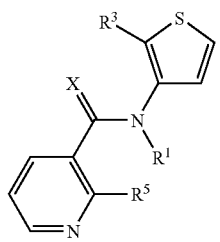

(It)

Table 21 provides 45 compounds of formula (Iu) where $R^1$, $R^3$, $R^5$ and X are as defined in Table 21.

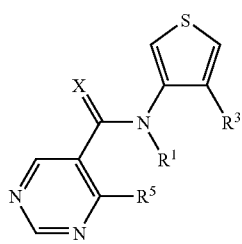

(Iu)

Table 22 provides 45 compounds of formula (Iv) where $R^1$, $R^3$, $R^5$ and X are as defined in Table 22.

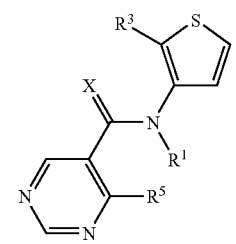

(Iv)

Table 23 provides 45 compounds of formula (Iw) where $R^1$, $R^3$, $R^5$ and X are as defined in Table 23.

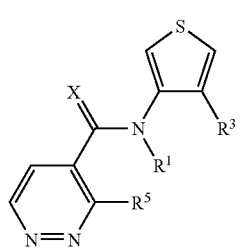

(Iw)

Table 24 provides 45 compounds of formula (Ix) where $R^1$, $R^3$, $R^5$ and X are as defined in Table 24.

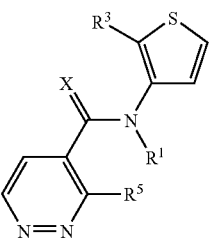

(Ix)

Table 25 provides 10 compounds of formula (Iy) where $R^7$ and $(R^2)_r$ are as defined in Table 25.

(Iy)

TABLE 25

| Compound Number | $R^7$ | $(R^2)_r$ |
|---|---|---|
| 25.1 | $CF_3$ | 2-Cl |
| 25.2 | $CF_3$ | 5-Cl |
| 25.3 | $CF_3$ | 2-Br |
| 25.4 | $CF_3$ | 5-Br |
| 25.5 | $CF_2H$ | 2-Cl |
| 25.6 | $CF_2H$ | 5-Cl |
| 25.7 | $CF_2H$ | 2-Br |
| 25.8 | $CF_2H$ | 5-Br |
| 25.9 | $CF_3$ | 2-Cl, 5-Cl |
| 25.10 | $CF_2H$ | 2-Cl, 5-Cl |

Table 26 provides 10 compounds of formula (Iz) where $R^7$ and $(R^2)_r$ are as defined in Table 26.

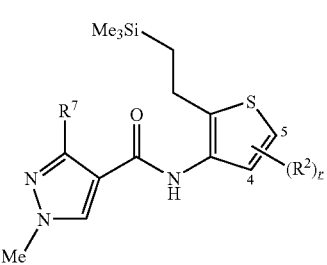

(Iz)

TABLE 26

| Compound Number | $R^7$ | $(R^2)_r$ |
|---|---|---|
| 26.1 | $CF_3$ | 4-Cl |
| 26.2 | $CF_3$ | 5-Cl |
| 26.3 | $CF_3$ | 4-Br |
| 26.4 | $CF_3$ | 5-Br |
| 26.5 | $CF_3$ | 4-Cl, 5-Cl |
| 26.6 | $CF_2H$ | 4-Cl |

TABLE 26-continued

| Compound Number | $R^7$ | $(R^2)_r$ |
|---|---|---|
| 26.7 | $CF_2H$ | 5-Cl |
| 26.8 | $CF_2H$ | 4-Br |
| 26.9 | $CF_2H$ | 5-Br |
| 26.10 | $CF_2H$ | 4-Cl, 5-Cl |

Table G represents Table 27 (when G is 27) and represents Table 28 (when G is 28).

TABLE G

| Compound Number | $R^3$ | A |
|---|---|---|
| G.1 | $(CH_2)_2SiMe_3$ | $NH_2$ |
| G.2 | $(CH_2)_2SiMe_3$ | NHCHO |
| G.3 | $(CH_2)_2SiMe_3$ | $NHCOOC(CH_3)_3$ |
| G.4 | $(CH_2)_2SiMe_3$ | Br |
| G.5 | $(CH_2)_2SiMe_3$ | $N=C(C_6H_5)_2$ |
| G.6 | $(CH_2)_2SiMe_3$ | $NHCOC(CH_3)_3$ |
| G.7 | $CHMeCH_2SiMe_3$ | $NH_2$ |
| G.8 | $CHMeCH_2SiMe_3$ | NHCHO |
| G.9 | $CHMeCH_2SiMe_3$ | $NHCOOC(CH_3)_3$ |
| G.10 | $CHMeCH_2SiMe_3$ | Br |
| G.11 | $CHMeCH_2SiMe_3$ | $N=C(C_6H_5)_2$ |
| G.12 | $CHMeCH_2SiMe_3$ | $NHCOC(CH_3)_3$ |
| G.13 | $SiMe_3$ | NHCHO |
| G.14 | $SiMe_2CH_2CHMe_2$ | NHCHO |

Table 27 provides 14 compounds of formula (IIa) where $R^3$ and A are as defined in Table 27.

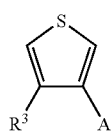

(IIa)

Table 28 provides 14 compounds of formula (IIb) where $R^3$ and A are as defied in Table 28.

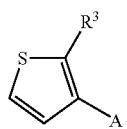

(IIb)

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

| m.p. = melting point | b.p. = boiling point. |
|---|---|
| s = singlet | br = broad |
| d = doublet | dd = doublet of doublets |
| t = triplet | q = quartet |

-continued

| m = multiplet | ppm = parts per million |
|---|---|
| qd = quartet of doublets | sext = sextet |

Table 29 shows selected melting point selected NMR data, all with $CDCl_3$ as the solvent (unless otherwise stated; if a mixture of solvents is present, this is indicated as, for example, ($CDCl_3/d_6$-DMSO)) and characteristic mass spectrum signals (no attempt is made to list all characterising data in all cases) for compounds of Tables 1 to 28.

TABLE 29

| Compound Number | $^1$H-NMR data: (ppm/multiplicity/number of Hs) or mass spectrum signal | m.p./ (° C.) |
|---|---|---|
| 1.14 | | 140-142 |
| 1.16 | | 145-147 |
| 2.1 | | 121-124 |
| 2.2 | | 85-88 |
| 2.14 | | 109-111 |
| 2.16 | | 140-142 |
| 2.72 | | 57-59 |
| 2.73 | | 70-71 |
| 2.75 | | 80-83 |
| 2.76 | | 74-76 |
| 2.84 | | 130-133 |
| 2.85 | $(M^++Cl): 420$ | |
| 6.1 | | 88-92 |
| 6.14 | | 74-77 |
| 6.47 | $(M^++H): 407$ | |
| 20.1 | 0.4(s, 9); 7.45(m, 1); 7.6(d, 1); 7.8(d, 1); 8.2(br, 1); 8.25(m, 1); 8.6(m, 1). | |
| 20.14 | | 106-110 |
| 27.2 | $(M^+-1): 226$ | |
| 27.4 | 0.0(s, 9); 0.8(m, 2); 2.6(m, 2); 6.9(d, 1); 7.2(d, 1) | 126-128 |
| 28.1 | 0.05(s, 9); 0.85(m, 2); 2.6(m, 2); 3.3(br.s, 2); 6.6(d, 1); 6.9(d, 1) | |
| 28.2 | | 52-53 |
| 28.3 | 0.0(s, 9); 0.9(m, 2); 1.4(s, 9); 2.6(m, 2); 6.0(br.s, 1); 7.0(m, 2) | |

The compounds according to the present invention may be prepared according to the following reaction schemes, in which, unless otherwise stated, the definition of each variable is as defined above for a compound of formula (I).

There are a number of alternative methods for preparing a compound of formula (I).

Method A

A compound of formula (I) may be prepared by reacting a compound of formula (IIa) or (IIb) [in which A is $NH_2$, NHCH(O), optionally substituted $(C_{1-4})$alkylC(=O)NH or optionally substituted $(C_{1-4})$alkylOC(=O)NH] with a compound of formula Het-C(=O)OR' [where R' is $C_{1-5}$ alkyl] in the presence of a strong base [for example NaH or sodium hexamethyldisilazane], in a dry polar solvent [preferably THF] and at a temperature between −10° C. and the boiling point of the solvent [preferably at ambient temperature]. The article by J. Wang et al [Synlett 2001, 1485] provides details of analogous preparations. When A is NHCH(O), optionally substituted $(C_{1-4})$alkylC(=O)NH or optionally substituted $(C_{1-4})$alkylOC(=O)NH; and a compound of formula (I) in which $R^1$ is H is desired, then hydrolysis according to Method E below must follow.

Method B

A compound of formula (I) may be prepared by reacting a compound of formula (IIa) or (IIb) [where A is as defined above in Method A] with a compound of formula Het-C(=O)R" [where R" is OH or a leaving group, such as Cl, Br, F or OC(=O)C$_{1-4}$ alkyl] in an inert organic solvent [such as ethylacetate, dichloromethane, dioxane, THF or DMF] and at a temperature between −10° C. and the boiling point of the solvent [preferably at ambient temperature]. If R" is OH, then the reaction is carried out in the presence of an activating agent [for example BOP—Cl] and two equivalents of a base [such as a tertiary amine, an inorganic carbonate or a hydrogen carbonate]. Alternatively, if R" is a leaving group, then the reaction is carried out in the presence of at least one equivalent of base [for example pyridine, a tertiary amine, an inorganic carbonate or a hydrogen carbonate; a stronger base, such as NaH or sodium hexamethyldisilazane is used when A is NHCH(O), optionally substituted (C$_{1-4}$)alkylC(=O)NH or optionally substituted (C$_{1-4}$)alkylOC(=O)NH]. If a compound of formula (I) in which R$^1$ is H is desired, then hydrolysis according to Method E must follow.

Method C

A compound of formula (I) [where R$^1$ is as defined above but is not hydrogen] may be prepared by reacting a compound of formula (I) [where R$^1$ is hydrogen] with a compound of formula R$^1$-L$^1$ [where R$^1$ is as defined above but is not hydrogen; and L$^1$ is a leaving group, such as Cl, Br, I, a sulfonate (for example a mesylate or a tosylate) or OC(O)C$_{1-4}$ alkyl] in a solvent [such as an halogenated solvent (for example dichloromethane), an ether, ethylacetate, DMF or even water (as a biphasic mixture, optionally in the presence of a phase transfer catalyst such as tetrabutylammonium hydrogensulfate)] and in the presence of a base [such as a tertiary amine, an alkali carbonate, an alkali bicarbonate, an alkali hydroxide or NaH; though when L$^1$ is O(CO)C$_{1-4}$ alkyl then simply heating without base is possible].

Method D

A compound of formula (I) may be prepared by reacting a compound of formula (IIa) or (IIb) [where A is halogen, preferably bromo or iodo] with a compound of formula Het-C(=O)NH$_2$ in the presence of a Cu(I) compound and an aprotic solvent [such as a cyclic ether, for example dioxane] at an elevated temperature and preferably at reflux. It is preferred that CuI is used at 2% to 100% mole/mole, relative to the compound of formula (IIb), in the presence of a 1,2-diamine (such as 1,2-diamino cyclohexane or ethylene diamine) as a ligand-forming substance and at least one equivalent of a base (such as an alkali carbonate or an alkali phosphate). The article by A. Klapars et al. J. Am. Chem. Soc. 123, 7727 (2001) provides details of analogous preparations.

Method E

A compound of formula (I) [where R$^1$ is H] may be prepared from a compound of formula (I) [where R$^1$ is as defined above, but is not H] by acidic or alkaline hydrolysis. For this purpose the compound is treated with aqueous acid or base, for example HCl, HBr or an organic hydroxide [such as sodium-, potassium-, calcium- or barium-hydroxide] in an appropriate solvent which is preferably mixable with water [for example THF, dioxane, a lower alcohol or water itself] at ambient or elevated temperatures.

Method F

A compound of formula (I) [where R$^1$ is H] may be prepared from a compound of formula (IIa) or (IIb) [where A is N=C(C$_6$H$_5$)$_2$] by converting A to NH$_2$, for example according to methods described by J. Ahman et al. Tetrahedron Letters 38, 6363 (1997) and proceeding according to Method A or Method B, preferably without isolation or purification of the intermediates:

Some compounds of formulae (IIa) and (IIb) are already known; novel compounds of formula (IIa) or (IIb) may be prepared according to the following synthetic strategies which are depicted in the following scheme and described below:

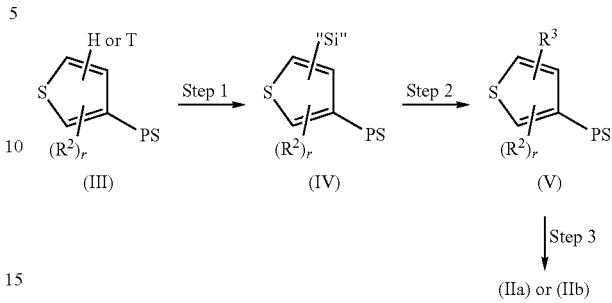

Step 1: Starting from a suitable precursor of formula (III) which carries a precursor substituent PS [which is a protected or free amino function, a substituent which may be converted to NH$_2$ in a later stage of the synthesis or a precursor group for A as defined above] and, optionally, a substituent T [which is convertible to "Si", a silicon containing substituent which is either R$^3$ as defined above or is a precursor for such R$^3$] an appropriate Si-containing functionality ("Si") is introduced into the ortho-position to give a compound of formula (IV).

Step 2: If necessary, the introduced "Si" group is further manipulated to form the desired substituent R$^3$ in a compound of formula (V).

Step 3: Deprotection if necessary or conversion of the precursor substituent to yield substituent A, giving a compound of formula (IIa) or (IIb).

Steps 2 and 3 may also be carried out in reversed order.

Examples of protecting groups for the NH$_2$ functionality are formyl, acyl, haloacyl, trialkylsilyl, (substituted)benzyl and alkoxycarbonyl. A more comprehensive list of methods for protection and deprotection of aromatic and heteroaromatic amines which are useful in the context of the present invention may be found in T. W. Green and P. G. M. Wuts, Protective Groups in Organic Synthesis 3$^{rd}$ edition p. 503-614 (Wiley 1999).

Examples for precursor substituents PS are nitro and azido [both of which may be converted to NH$_2$ by reduction or hydrogenation], carboxyl and carboxy derivatives [which may undergo rearrangements to form isocyanates, for example by Curtius-, Schmidt- or Hofmann-degradation] and halides and triflates [which may be converted to NH$_2$ in protected or unprotected form via palladium catalysed amination reactions currently known under the name "Buchwald Hartwig" reaction, see for example J. Ahman et al. Tetrahedron Letters 38, 6363 (1997) and X. Huang et al., Org. Lett. 3, 3417 (2001) and references cited therein].

More comprehensive lists for useful precursor substituents for NH$_2$ may be found in Rodd's Chemistry of Carbon Compounds III B and its supplements (Elsevier 1974, 1981 and 1995) and in Compendium of Organic Synthetic Methods Vols. 1-9 chapter 7 (Wiley 1971-2000).

For the introduction of Si-containing functionalities into thienyl derivatives (step 1) a large variety of synthetic methods are accessible. The chemist skilled in the art will understand that according to the methodology chosen for step 1 different groups T may be used. Examples of useful T substituents are halogens (such as Cl, Br and I), sulfonates (such as triflates, tosylates and mesylates), phosphates, C$_{1-4}$ alkyl, C$_{2-4}$ alkenyl and C$_{2-4}$ alkynyl.

Manipulation of Si-containing functional groups (step 2) is widely known in the literature. Recent overviews may be found in The Chemistry of Organosilicon Compounds, Vols. 1-3, S. Patay, Z. Rappaport and Y. Apeloig eds. Wiley, 1989, 1998, 2001 and in Houben-Weyl Science of Synthesis, Organometallics Vol. 4, I. Fleming ed., G. Thieme 2002. Examples of manipulations which are especially relevant to the present invention are hydrogenation or reduction of double or triple bonds (or both) in the Si-containing group (see Example 3, step B below), and functional group manipulation on the silicon atom (for example conversion of halogens to alkyl or alkoxy groups).

Literature examples which illustrate some of the methods which may be used with appropriate modification of Step 1 in the above reaction scheme and which are therefore especially relevant to the preparation of compounds of formula (IIa) and (IIb) include Tetrahedron 57, 5339 (2001); Tetrahedron 56, 2985 (2000); Tetrahedron 46, 2632 and 2632 (1990); WO94/12505; J. Org. Chem. 64, 2471 (1999); J. Org. Chem. 55, 2993 (1990); J. Org. Chem. 51, 5286 (1986); U.S. Pat. No. 4,777, 262; Zh. Obschei Khimi, 52, 2767 (1982); Chemica Scripta 18, 192 (1981), J. Med. Chem. 45, 3022 (2002); A. R. M. Allison et al., Tetrahedron Letters 35, 4425 (1994); Tetrahedron Letters 25, 81 and 83 (1984); Tetrahedron Letters 30, 3735 (1989); Chemistry Letters 2001, 386; Chemistry Letters 1990, 2175 and references cited therein.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, for example, from phytopathogenic microorganisms.

It is also possible to use compounds of formula (I) as dressing agents for the treatment of plant propagation material, in particular of seeds (fruit, tubers, grains) and plant cuttings (for example rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (for example *Botrytis, Pyricularia, Helminthosporium, Fusarium, Septoria, Cercospora* and *Altemaria*) and *Basidiomycetes* (for example *Rhizoctonia, Hemileia, Puccinia*). Additionally, they are also effective against the Ascomycetes classes (for example *Venturia* and *Erysiphe, Podosphaera, Monilinia, Uncinula*) and of the Oomycetes classes (for example *Phytophthora, Pythium, Plasmopara*). Outstanding activity has been observed against powdery mildew (*Erysiphe* spp.). Furthermore, the novel compounds of formula I are effective against phytopathogenic bacteria and viruses (for example against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations, for example, in polymeric substances. As with the type of the compositions, the methods of application, such as spraying, atomising, dusting, scattering, coating or pouring, are chosen in accordance with the intended objectives and the prevailing. circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, for example, natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds may be, for example, fertilizers or micronutrient donors or other preparations which influence the growth of plants. They may also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, for example, in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound Numbers 27.2 and 1.14.

Step A

4-Bromo-3-thiophene carboxylic acid (prepared according to J. Heterocyclic Chem. 1999, 36, 761) (2 g), triethylamine (1.5 g) and acetone (15 ml) were cooled to −10° C. and ethylchloroformiate (1.15 g) was added at this temperature. The reaction mixture was stirred at room temperature for 2 hours, cooled to 0° C. and sodioum azide (0.97 g) dissolved in water (5 ml) was added slowly. After 2 hours at room temperature the mixture was filtered, the acetone was evaporated and the residue was diluted with dichloromethane, washed with water and dried over sodium sulfate. Evaporation of the solvent yielded 1.7 g of an off-white powder which was directly used in the next step Step B: 4-Bromo-3-thiophene-formamide Formic acid (30 ml) was heated to reflux and the product of Step A, dissolved in formic acid (10 ml), was added dropwise. The mixture was heated for 30 minutes until gas evolution stopped. The formic acid was removed under vacuum and then the residue was diluted with ethyl acetate and washed with saturated sodium bicarbonate solution. After drying and removal of the solvent the product was chromatographed on silica gel (hexane:ethylacetate 2:1) to yield 1.1 g of product (m.p. 108-110° C.).

Step C: 4-(Trimethylsilyl)ethinyl-3-thiophene formamide

The product from step B (1 g), tributylstannyl(trimethylsilyl)acetylene (2.16 g) and palladium(tetrakis)triphenylphoshine (0.28 g) were placed into degassed toluene (20 ml) and the mixture was heated under reflux for 16 hours under an atmosphere of nitrogen. After cooling, the solvent was removed and the residue was chromatographed on silica gel (hexane:ethylacetate 3:1). After three consecutive crystallisations from hexane, 0.3 g of 4-(trimethylsilyl)ethinyl-3-thiophene formamide was obtained (m.p. 90-94° C.).

Step D: Compound Number 27.2

The product obtained from step C was hydrogenated in THF over Pd on charcoal (10%) (0.3 g) until hydrogen uptake stopped. Evaporation of the solvent yielded Compound Number 27.2 (0.28 g).

Step E: Compound Number 1.14

Sodium hydride (0.06 g) was dispersed in THF (10 ml) and the mixture was cooled with an ice bath. Compound Number 27.2 (0.14 g), dissolved in THF (5 ml), was added and the suspension was stirred at 0-5° C. for 30 minutes. N-Methyl-3-trifluoromethyl-4-chlorocarbonyl-pyrazole (0.2 g) was added at this temperature and the reaction mixture was stirred at room temperature overnight. The reaction mixture was poured on to water and was extracted with ethylacetate. The organic phase was washed with water, dried over sodium sulfate and the solvent was evaporated. The residue was treated with an excess of sodium methylate in methanol and then, after 15 minutes at room temperature, the mixture was acidified with HCl and extracted with ethyl acetate. After washing with saturated sodium bicarbonate, drying over sodium sulfate and removing the solvent, the residue was chromatographed on silica gel (hexane:ethyl acetate 1:1) and recrystallised from hexane, yielding Compound Number 1.14 (0.072 g).

EXAMPLE 2

This Example illustrates the preparation of Compound Numbers 28.2, 2.85 and 2.16.

Step A: 2-Iodo-3-formylaminothiophene

3-Formylamino-thiophene (21 g), N-iodosuccinimide (37.2 g) and tetrachlormethane (200 ml) were refluxed together for 3 hours. The reaction mixture was cooled to 0-5° C. and filtered. The solids were dissolved in ethyl acetate, washed three times with sodium hydroxide (10% solution), washed with brine and dried over sodium sulfate. Evaporation of the solvents and chromatography of the residue over silica gel (hexane:ethyl acetate 2:1) yielded 37.8 g of product (m.p. 100-107° C.) which was directly used in Step B.

Step B: 2-(Trimethylsilylethinyl)-3-formamido-thiophene.

The product from step A (37.8 g) was dissolved in a mixture of DMF (500 ml) and triethylamine (50 ml). CuI (1.4 g) and bis(triphenylphosphino)palladiumdichloride (5.2 g) were added under nitrogen and after 15 minutes ethinyl trimethylsilane (22 g) was added dropwise. After 6 hours the solvents were removed under vacuum and the residue was chromatographed on silica gel (hexane:ethyl acetate 2:1) to yield 2-(trimethylsilylethinyl)-3-formamido-thiophene (31.78 g) (m.p. 87-93° C.).

Step C: Compound Number 28.2

Hydrogenation of the product from Step B (31.78 g) in THF over Pd (30 g) on charcoal, as described for Compound Number 27.2 in Step D of Example 1, yielded Compound Number 28.2 (26.3 g).

Step D: Compound Numbers 2.85 and 2.16

Compound 28.2 (23.4 g) was treated with sodium hydride (7.4 g) and N-methyl-3-difluoromethyl-4-chlorocarbonyl pyrazole (30 g) as described in Step E of Example 1, to form a reaction mixture.

In order to prepare Compound Number 2.85, one tenth of the reaction mixture was poured on to water and was extracted with ethylacetate. The organic phase was washed with water, dried over sodium sulfate and the solvent was evaporated. The residue was chromatographed on silica gel (hexane:ethylacetate 1:1) and Compound Number 2.85 was isolated by removal of the solvent; yield: 0.6 g.

In order to prepare Compound Number 2.16, the reaction mixture was treated with sodium hydroxide (100 ml of a 10% w/w solution in water) and stirred over night. The reaction mixture was diluted with saturated ammonium chloride solution, extracted with ethyl acetate, dried over sodium sulfate and the solvent was removed under reduced pressure. The residue was recrystallised with hexane:toluene (3:1) to yield Compound Number 2.16 (27.7 g).

EXAMPLE 3

This Example illustrates the preparation of Compound Number 6.1.

Step A

3- Formylaminothiophene (Bull. Soc. Chim. Fr. 1976,151) (2 g), dissolved in dry THF (20 ml), was dropped into a freshly prepared solution of lithium diisopropylamine (0.035 mol) in THF (35 ml) at −70° C. The solution was warmed to −20° C. and stirred for 30 minutes, then cooled again to −70° C., whereupon trimethylsilylchloride (5 ml) was added. After stirring for an additional hour at this temperature the mixture was slowly warmed to room temperature and stirred for 4 hours. Quenching with a saturated solution of ammonium chloride, extracting with ethyl acetate, drying over sodium sulfate, removing the solvent and applying chromatography on silica gel (hexane:ethyl acetate 2:1) yielded 2-trimethyl-silyl-3-formylaminothiophene (1.2 g) (m.p. 74-76° C.).

Step B: Compound Number 6.1

Preparation of Compound Number 6.1 was carried out according to Step D of Example 2 using the above intermediate from Step A (0.4 g), sodium hydride (0.13 g), 2-methyl-4-trifluormethyl-5-chlorocarbonyl-thiazole (0.69 g) and sodium hydroxide solution (1.5 ml of a 2 molar solution). Chromatography on silica gel hexane:ethyl acetate 4:1) yielded Compound Number 6.1 (0.29 g).

FORMULATION EXAMPLES FOR COMPOUNDS OF FORMULA (I)

Working procedures for preparing formulations of the compounds of formula I such as Emulsifiable concentrates, Solutions, Granulates, Dusts and Wettable powders are described in WO 97/33890.

BIOLOGICAL EXAMPLES: FUNGICIDAL ACTIONS

Example B-1

Action Against *Puccinia recondita*/Wheat (Brownrust on Wheat)

1 week old wheat plants cv. Arina were treated with the formulated test compound (0.02% active ingredient) in a spray chamber. One day after application wheat plants were inoculated by spraying a spore suspension ($1 \times 10^5$ uredospores/ml) on the test plants. After an incubation period of 2 days at 20° C. and 95% r.h. plants were kept in a greenhouse for 8 days at 20° C. and 60% r.h. The disease incidence was assessed 10 days after inoculation.

Infestation was prevented virtually completely (0-5% infestation) with each of Compounds 1.14, 1.16, 2.1, 2.2, 2.14, 2.16, 2.75, 2.76, 2.84, 2.85 and 6.01.

Example B-2

Action Against *Podosphaera leucotricha*/Apple (Powdery Mildew on Apple)

5 week old apple seedlings cv. McIntosh were treated with the formulated test compound (0.002% active ingredient) in a spray chamber. One day after application apple plants were inoculated by shaking plants infected with apple powdery mildew above the test plants. After an incubation period of 12 days at 22° C. and 60% r.h. under a light regime of 14/10 hours (light/dark) the disease incidence was assessed.

Compounds 2.14 and 2.16 each exhibited strong efficacy (<20% infestation).

Example B-3

Action Against *Venturia inaequalis*/Apple (Scab on Apple)

4 week old apple seedlings cv. McIntosh were treated with the formulated test compound (0.02% active ingredient) in a spray chamber. One day after application apple plants were inoculated by spraying a spore suspension ($4 \times 10^5$ conidia/ml)

on the test plants. After an incubation period of 4 days at 21° C. and 95% r.h. the plants were placed for 4 days at 21° C. and 60% r.h. in a greenhouse. After another 4 day incubation period at 21° C. and 95% r.h. the disease incidence was assessed.

Compounds 2.14 and 2.16 each exhibited strong efficacy (<20% infestation).

Example B-4

Action Against *Erysiphe graminis*/Barley (Powdery Mildew on Barley)

1 week old barley plants cv. Express were treated with the formulated test compound (0.02% active ingredient) in a spray chamber. One day after application barley plants were inoculated by shaking powdery mildew infected plants above the test plants. After an incubation period of 6 days at 20° C./18° C. (day/night) and 60% r.h. in a greenhouse the disease incidence was assessed.

Compounds 1.14, 1.16, 2.14, 2.16, 2.75, 2.76 and 2.85 each exhibit strong efficacy (<20% infestation).

Example B-5

Action Against *Botrytis cinerea*/Tomato (*Botrytis* on Tomatoes)

4 week old tomato plants cv. Roter Gnom were treated with the formulated test compound (0.02% active ingredient) in a spray chamber. Two days after application tomato plants were inoculated by spraying a spore suspension ($1 \times 10^5$ conidia/ml) on the test plants. After an incubation period of 4 days at 20° C. and 95% r.h. in a growth chamber the disease incidence was assessed.

Compounds 1.14, 1.16, 2.14, 2.16, 2.75, 2.76 and 2.85 each exhibit strong efficacy (<20% disease incidence).

Example B-6

Action Against *Septoria nodorum*/Wheat (*Septoria* Leaf Spot on Wheat)

1 week old wheat plants cv. Arina were treated with the formulated test compound (0.02% active ingredient) in a spray chamber. One day after application wheat plants were inoculated by spraying a spore suspension ($5 \times 10^5$ conidia/ml) on the test plants. After an incubation period of 1 day at 20° C. and 95% r.h. plants are kept for 10 days at 20° C. and 60% r.h. in a greenhouse. The disease incidence was assessed 11 days after inoculation.

Compounds 1.14, 1.16, 2.14, 2.16, 2.75, 2.76 and 2.85 each show good activity in this test (<60% disease incidence).

What is claimed is:

1. A compound of formula (I)

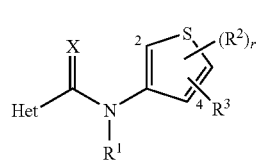

where Het is a 5- or 6-membered heterocyclic ring containing one to three heteroatoms, each independently selected from oxygen, nitrogen and sulphur, the ring being substituted by one to three groups $R^4$; $R^1$ is hydrogen, optionally substituted ($C_{1-4}$)alkyl, formyl, optionally substituted ($C_{1-4}$)alkylC(=O), optionally substituted ($C_{1-4}$)alkylC(=O)O, optionally substituted ($C_{1-4}$)alkoxy($C_{1-4}$)alkyl, optionally substituted allyl, optionally substituted propargyl or optionally substituted allenyl; each $R^2$ is, independently, halogen, optionally substituted ($C_{1-4}$)alkyl, optionally substituted ($C_{1-4}$)alkoxy or optionally substituted ($C_{1-4}$)alkoxy($C_{1-4}$)alkyl; $R^3$ is either at position 2 or at position 4 of the thiophene ring and is an organic group containing three to thirteen carbon atoms and at least one silicon atom and, optionally, one to three heteroatoms, each independently selected from oxygen, nitrogen and sulphur, and is optionally substituted by one to four independently selected halogen atoms; each $R^4$ is, independently, halogen, $C_{1-3}$ alkyl, $C_{1-3}$ haloalkyl, $C_{1-3}$alkoxy($C_{1-3}$)alkyl or cyano; r is 0, 1 or 2; and X is O or S; or an N-oxide thereof.

2. A compound of formula (I) as defined in claim 1 provided that the Het ring is not 1,2,3-triazole when X is O.

3. A compound of formula (I) as defined in claim 1 where $R^1$ is hydrogen, propargyl, allenyl, formyl, $CH_3C(=O)$, $C_2H_5C(=O)$ or $CH_3OCH_2C(=O)$.

4. A compound of formula (I) as defined in claim 1 where each $R^2$ is independently selected from halogen, methyl, trifluoromethyl and trifluoromethoxy.

5. A compound of formula (I) as defined in claim 1 where Het is pyrazolyl, pyrrolyl, thiophenyl, furyl, thiazolyl, isothiazolyl, oxazolyl, isoxazolyl, triazolyl, pyridinyl, pyrazinyl, pyrimidinyl, pyridazinyl, 5.6-dihydropyranyl or 5.6-dihydro-1.4-oxathiinyl each being substituted by one to three groups $R^4$.

6. A compound of formula (I) as defined in claim 1 where $R^3$ is an aliphatic, saturated or unsaturated group containing three to thirteen carbon atoms and at least one silicon atom and, optionally, one to three heteroatoms, each independently selected from oxygen, nitrogen and sulphur, and is optionally substituted by one to four independently selected halogen atoms.

7. A compound of formula (I) as defined in claim 1 where X is oxygen.

* * * * *

UNITED STATES PATENT AND TRADEMARK OFFICE
CERTIFICATE OF CORRECTION

PATENT NO. : 7,582,589 B2 Page 1 of 1
APPLICATION NO. : 10/554336
DATED : September 1, 2009
INVENTOR(S) : Ehrenfreund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this

Fourteenth Day of September, 2010

David J. Kappos
*Director of the United States Patent and Trademark Office*